United States Patent [19]

Meezan et al.

[11] Patent Number: 5,817,634
[45] Date of Patent: Oct. 6, 1998

[54] METHODS OF TREATING DIABETES MELLITUS AND CLYCOGEN STORAGE DISEASE

[75] Inventors: Elias Meezan; Stephen M. Manzella, both of Birmingham, Ala.

[73] Assignee: The UAB Research Foundation, Birmingham, Ala.

[21] Appl. No.: 364,501

[22] Filed: Dec. 27, 1994

Related U.S. Application Data

[63] Continuation of Ser. No. 28,970, Mar. 10, 1993, abandoned.
[51] Int. Cl.$^6$ .................. A61K 31/70; A61K 31/705; C07H 7/02
[52] U.S. Cl. .................. 514/24; 514/25; 514/54; 514/61; 514/866; 536/4.1; 536/18.6; 536/123.1; 536/123.13; 536/123; 536/17.2; 252/174.17
[58] Field of Search .................. 514/24, 25, 54, 514/866, 61; 536/4.1, 18.6, 123.1, 123.13, 123, 17.2; 252/174.17

[56] References Cited

U.S. PATENT DOCUMENTS

| | | | |
|---|---|---|---|
| H171 | 12/1986 | McDaniel et al. | 252/174.17 |
| 3,547,828 | 12/1970 | Mansfield et al. | 252/351 |
| 3,586,664 | 6/1971 | Kohno et al. | 536/4.1 |
| 4,454,123 | 6/1984 | Noyori et al. | 424/180 |
| 4,690,775 | 9/1987 | Schott et al. | 252/312 |
| 4,868,289 | 9/1989 | Magnusson et al. | 536/4.1 |
| 4,877,808 | 10/1989 | Samreth et al. | 514/432 |
| 5,166,337 | 11/1992 | Ripke | 536/126 |

FOREIGN PATENT DOCUMENTS 3188094  8/1991  Japan .

OTHER PUBLICATIONS

Yamanouchi, K. et al., "Metabolic Effects of Proglycosyn," *Arch. Biochem. Biophys.*, 294(2):609–615 (May 1, 1992).

Vaag, A. et al., "Effect of Acute Hyperglycemia on Glucose Metabolism in Skeletal Muscles in IDDM Patients," *Diabetes*, 41:174–182 (Feb. 1992).

Zhehavi U. et al., "Polymers having (1→4)–and (1→6)–linked α–D–glucopyranosyl Groups as Acceptors in the Glycogen Synthase Reaction," *Carbohydr. Res.*, 228:225–263 (1992).

Guo, Z. K. et al., "Stimulation of Glycogen Synthesis by Proglycosyn (LY177507) by Isolated Hepatocytes of Normal and Streptozotocin Diabetic Rats," *J. Biol. Chem.*, 266:22323–22327 (1991).

Smythe, C. et al., "The Discovery of Glycogenin and the Priming Mechanism for Glycogen Biogenesis," *Eur. J. Biochem.*, 200:625–631 (1991).

Gressner, A. M., "Questioning The Reliability of ρ–Nitrophenyl–β–D–xyloside as Probe to Study the Metabolic Effects of Abrogated Proteoglycan Synthesis in Cultured Cells," *Biochem. Pharm.*, 42:1987–1995 (1991).

Lomako, J. et al., "Substrate Specificity of the Autocatalytic Protein that Primes Glycogen Synthesis," *FEBS Lett.*, 264:13–16 (1990).

Bogardus, C. et al., "Where all the Glucose Doesn't go in Non–insulin–dependent Diabetes Mellitus," *N. Eng. J. Med.*, 322(4):262–263 (Jan. 25, 1990).

Shulman, G. I. et al., "Quantitation of Muscle Glycogen Synthesis in Normal Subjects and Subjects with Non–insulin–dependent Diabetes by $^{13}$C Nuclear Manetic Resonance Spectroscopy," *N. Eng. J. Med.*, 322(4):223–228 (Jan. 25, 1990).

Harris, R. A. et al., "Stabilization of Glycogen Stores and Stimulation of Glycogen Synthesis in Hepatocytes by Phenacyl Compounds," *J. Biol. Chem.*, 264:14674–14680 (1989).

Zhehavi, U. et al., "Probing Acceptor Specificity in the Glycogen Synthase Reaction with Polymer–Bound Oligosacchrides," *Carbohydr. Res.*, 151:371–378 (1986).

Weber, N. et al., "Metabolism of Orally Adminstered Alkyl βGlycosides in the Mouse," *J. Nutr.*, 114:247–254 (1984).

Durette et al, "Structure–Activity Relationships of Aminalkyl and –aryl Glycosides Having Insulin–like activity," Jour. Med. Chem. 21(9): pp. 854–859 (1978).

*Primary Examiner*—Francisco C. Prats
*Attorney, Agent, or Firm*—Benjamin Aaron Adler, I.D.

[57] ABSTRACT

This present invention provides a method and compounds for priming the incorporation of cellular glucose into an oligosaccharide in a cell comprising administering to the cell a priming amount of a membrane-permeating nontoxic glycoside having a suitable hydrophobic organic group joined by a linkage to a suitable hydrophilic saccharide, wherein the hydrophilic saccharide has a nonreducing terminal sugar residue selected from the group consisting of glucose or xylose, thereby priming the incorporation of cellular glucose onto the glycoside to form an oligosaccharide. Also disclosed are methods wherein the administration of the glycoside is sufficient to treat diabetes mellitus and glycogen storage disease.

17 Claims, No Drawings

METHODS OF TREATING DIABETES MELLITUS AND CLYCOGEN STORAGE DISEASE

This application is a continuation of application Ser. No. 08/028,970, filed Mar. 10, 1993, now abandoned.

BACKGROUND OF THE INVENTION

1. Field of the Invention

The instant invention relates to a method of priming the incorporation of glucose into an oligosaccharide having $\alpha(1\rightarrow 4)$ glycosidic linkages. In particular, the invention relates to a method of treating diabetes mellitus.

2. Background Art

Diabetes mellitus is a common, widespread disease syndrome best characterized by hyperglycemia due to an absolute or relative lack of insulin (Diabetes Mellitus, Theory and Practice, 3d Ed., M. Ellenberg and H. Rifkin, eds., Medical Examination Publishing Co., New Hyde Park, 1983). Hyperglycemia is accompanied by altered metabolism of carbohydrates, lipids and proteins, and although the disease can be controlled by dietary treatment, insulin and oral hypoglycemic agents, there is a substantial incidence of vascular complications in long-term diabetes which continues to be a significant cause of morbidity and mortality in this disease. Diabetic patients can generally be clinically placed into one of two major subtypes of the disease, insulin-dependent diabetes mellitus (IDDM or Type-I diabetes) or non-insulin-dependent diabetes mellitus (NIDDM or Type-II diabetes). Although the incidence of these two types of diabetes varies widely throughout the world, in the United States about 90% of diabetic patients have Type II diabetes with most of the remainder being classified as Type-I. Both Type-I and Type-II diabetes have a complex pathogenesis which is contributed to by both genetic and environmental factors.

Type-I diabetes mellitus appears to be an autoimmune disease of the pancreatic B cell in which this cell type is largely destroyed leading to a chronic state of insulin deficiency and consequent hyperglycemia. In contrast, Type-II diabetics show no significant loss of pancreatic B cells and have normal or even elevated levels of plasma insulin. Nevertheless, these patients are relatively insulin-deficient, because their B cells do not respond adequately to hyperglycemia by releasing enough insulin to maintain euglycemia. Therefore, the central characteristic of both types of diabetes mellitus is hyperglycemia.

The consequences of chronic hyperglycemia to body metabolism are complex. It is becoming increasingly clear, however, that the major factor responsible for the development of most of the long-term complications of diabetes is the toxic effect of prolonged exposure of diabetic tissues to elevated levels of glucose. Tissues dispose of glucose primarily by oxidizing it to carbon dioxide and water or by converting it to lactate and/or glycogen by nonoxidative pathways. In humans, it has recently been shown (Shulman, G. I. et al., *New Engl. J. Med.*, 322:223–228 (1990)) that the synthesis of muscle glycogen accounts for most of the total body glucose uptake and for all of the non-oxidative glucose metabolism in both normal and diabetic subjects. In the most prevalent form of diabetes mellitus, NIDDM, insulin resistance appears to be due to a defect in the pathway of glycogen synthesis in skeletal muscle (Bogardus, C. and Lillioja, S., *New Engl. J. Med.*, 322:262–263 (1990)). Glycogen metabolism has also been shown to be impaired in the skeletal muscle of IDDM patients so that the synthesis of this glucose storage compound is inadequate to meet the demands of hyperglycemia, resulting in an accumulation of glucose and its metabolites in muscle cells (Vaag, A. et al., *Diabetes*, 41:174–182 (1992)). Therefore, impaired utilization of glucose via its incorporation into macromolecular glycogen appears to be a common metabolic defect found in both Type-I and Type-II diabetes mellitus.

The regulation of glycogen metabolism is complex and is influenced by a variety of factors (Hers, H. G., et al., *The Metabolic Basis of Inherited Disease*, C. R. Scriver, A. L. Beaudet, W. S. Sly and D. Valle, eds. McGraw-Hill, N.Y., pp. 425–452 (1989)). Existing therapies for Type-I and Type-II diabetes mellitus are not specifically directed at influencing the glycogen biosynthetic pathway.

Glycogen storage disease is another group of disorders involving abnormalities in the metabolism of glycogen. The disease has various forms, each of which has a different enzymatic basis. The end result, however, is always accumulation of glycogen in the cells and its resulting pathologic consequences. The liver is a major organ of glycogen synthesis and storage. Because endogenous levels of glycogenin are significantly lower in liver than in muscle, liver glycogen is much larger than muscle glycogen. The pathologic consequences of glycogen storage disease are manifested most markedly in liver, even though muscle and other tissues are also involved in this disease. (Hers, H. G. et al., "Glycogen Storage Diseases" in *The Metabolic Basis of Inherited Disease* (C. R. Scriver, A. L. Beaudet, W. S. Sly and D. Valle, eds.) McGraw-Hill, N.Y., pp. 425–452 (1989)). The large size of the liver glycogen molecule may contribute to the major involvement of this organ in glycogen storage disease. Although various therapeutic approaches have been used in the treatment of the different forms of glycogen storage disease, the major intervention in this disease remains dietary manipulation (Moses, S. W., *J. Pediat. Gastroenterol. Nutr.*, 11:155–174 (1990)). Pharmacologic agents have also been used to a limited extent. There is a need for new types of agents to treat this severe disease syndrome.

Glycogenin is a self-glycosylating protein which serves an integral role in the biosynthesis of glycogen by creating a protein-linked malto-oligosaccharide primer upon which glycogen synthase and branching enzyme build the macromolecular glycogen molecule (Smythe, C. et al., *Eur. J. Biochem.*, 200:625–631 (1991)). The glycogenin protein, by an unknown mechanism, becomes self-glycosylating and is capable of elongating the initial mono- or disaccharide moiety to a linear oligosaccharide chain using UDP glucose as the donor substrate. This fully glycosylated form of glycogenin then serves as the oligosaccharide primer to initiate chain elongation by glycogen synthase. Glycogenin also has the interesting ability to use UDP xylose as a donor substrate (Roden, E. et al., *Abstracts of the 6th Congress of the Pan-American Association of Biochemical Societies*, (1990)), and indeed xylose incorporation into glycogen has been reported in studies of proteoglycan synthesis in chick embryo chondrocyte microsomal preparations (Kimura, J. H. et al., *Arch. Biochem. Biophys.*, 191:687–697 (1978)).

Although it is not clear whether the mechanism of self-glucosylation by glycogenin is intra or intermolecular, the enzyme is capable of transfer to exogenous substrates (Lomako, J. et al., *FEBS Lett.*, 264:13–16(1990) using p-nitrophenyl glucoside and p-nitrophenyl linked maltooligosaccharides. Such p-nitrophenyl saccharides, however, have a lower affinity for glycogenin and can be hydrolyzed to potentially toxic products such as p-nitrophenol (Gressner, A. M. et al., *Biochem. Pharm.*, 42:1987–1995

(1991)). Polymers having maltose and maltotriose side chains have also been shown to act as primers to elicit the de novo synthesis of glycogen (Zehavi, U. and Herchman, M., *Carbohydr. Res.* 151:371–378 (1986) and Zehavi, et al., *Carbohydr. Res.* 228: 255–263 (1992)). These polymers, however, are insoluble and cannot permeate cell membranes. Other stimulators of glycogen synthesis such as proglycosyn have been reported (Harris, R. A. et al., *J. BioL Chem.*, 264:14674–14680 (1989), Guo, Z. K. et al., *J. Biol. Chem.*, 266:22323–22327 (1991) and Yamanouchi, K. et al., *Arch. Biochem. Biophys.*, 294:609–615 (1992)), but they do not act as primers.

Thus, there exists an important need for a treatment that increases glucose utilization via the glycogen biosynthetic pathway and thereby can be used to treat both Type-I and Type-II diabetes mellitus and glycogen storage disease. Such a treatment would be most beneficial if it was compatible and synergistic with existing therapies for these diseases and if it were nontoxic.

SUMMARY OF THE INVENTION

The present invention provides a method of priming the incorporation of cellular glucose into an oligosaccharide in a cell comprising administering to the cell a priming amount of a membrane-permeating nontoxic glycoside having a suitable hydrophobic organic group joined by a linkage to a suitable hydrophilic saccharide, wherein the hydrophilic saccharide has a nonreducing terminal sugar residue selected from the group consisting of glucose or xylose, thereby priming the incorporation of cellular glucose onto the glycoside to form an oligosaccharide.

The invention further provides a method of treating diabetes mellitus by priming the incorporation of cellular glucose into an oligosaccharide.

The present invention also provides a method of treating glycogen storage disease by priming the incorporation of cellular glucose into an oligosaccharide.

The invention further provides an alkyl glycoside having an 8 to 14 carbon alkyl chain joined by a linkage to a saccharide having from four to eight glucose residues, wherein the linkage is selected from the group consisting of a glycosidic linkage and a thioglycosidic linkage.

The invention also provides an alkyl glycoside having an 8 to 14 carbon alkyl chain joined by a linkage to a saccharide having from one to eight glucose residues and a nonreducing terminal sugar residue consisting of xylose, wherein the linkage is selected from the group consisting of a glycosidic linkage and a thioglycosidic linkage.

The present invention also provides a method for assaying for the presence of glycogen synthesis enzymatic activity in a sample comprising a) incubating the sample with a composition comprising an alkyl glycoside having a nonreducing terminal glucose joined in a anomeric linkage, and radiolabeled UDP-glucose, and b) determining the presence of radioactivity incorporated into the alkyl glycoside, the presence of radioactivity indicating the presence of glycogen synthesis enzymatic activity in the sample.

Accordingly, the present invention also provides a method of and compounds for priming the incorporation of cellular glucose into an oligosaccharide.

The instant invention also provides alkyl glycoside compounds having an 8 to 14 carbon alkyl chain joined by a linkage to a saccharide having from 4 to 8 glucose residues and alkyl glycoside compounds having an 8 to 14 carbon alkyl chain joined by a linkage to a saccharide having from 1 to 8 glucose residues and a non-reducing sugar residue consisting of xylose.

The present invention still further provides methods for treating diabetes mellitus and glycogen storage disease.

Finally, the instant invention provides a method for assaying the presence of glycogen synthesis activity in a sample.

DETAILED DESCRIPTION OF THE INVENTION

The present invention may be understood more readily by reference to the following detailed description of specific embodiments and the Examples.

As used in the claims,"a" means one or more.

As used herein, a"suitable" group means one that, when a part of a particular glycoside molecule, will render the glycoside able to fulfill the limiting characteristics of the invention, i.e., that the glycoside is (1) able to prime the incorporation of glucose into an oligosaccharide within a cell; (2) nontoxic; and (3) membrane-permeating, i.e., having amphipathic properties which allow it to readily penetrate cells chemically intact so that it has access to glycogenin and glycogen synthase. Suitable compounds can be determined using the methods set forth in the examples."Nontoxic," as used herein, includes that the glycoside molecule has a sufficiently low toxicity to be suitable for human administration.

As used herein,"glycoside" refers to the condensation product of any sugar with any suitable hydrophobic organic group, involving the loss of at least the H of the hemiacetal OH of the sugar, and the formation of a linkage between the sugar and the organic group.

As used herein,"saccharide" is inclusive of monosaccharides, oligosaccharides or polysaccharides in straight chain or ring forms. Oligosaccharides are saccharides having two or more monosaccharide residues.

As used herein,"priming amount" means an amount or dose sufficient to prime the incorporation of cellular glucose into an oligosaccharide in a cell.

As used herein, methods performed"in a cell" indicate both in vitro and in vivo methods.

Maltose is a known disaccharide of glucose residues. Maltotriose has three glucose residues. Maltotetraose has four glucose residues. Other maltose derivatives are thusly named.

A"glycosidase inhibitor" refers to a compound which inhibits the hydrolysis of the glycosidic bond between two carbohydrates or a carbohydrate and the aglycone of a glycoside, an example of which is acarbose (Miles Laboratories, United States and Bayer, Germany).

A"hypoglycemic agent" refers to a compound which lowers plasma glucose levels, for example, tolbutamide and glyburide.

Also included herein is a method for assaying glycogen synthesis enzymatic activity in a sample. Such a"sample" can be a crude extract of a tissue or a cell culture or a more purified tissue or cell extract, as by affinity purification or by chromatofocusing. Glycosides useful for assaying include those useful for priming the incorporation of glucose into oligosaccharides, as it is the incorporation of radioactive forms of glucose into $\alpha(1\rightarrow4)$ glycosidic linkages in oligosaccharides that indicates the presence of such enzymatic activity. Examples of novel uses of glycosides for assaying glycogen synthesis enzymatic activity include using non-p-nitrophenyl compounds. This use is the first use of nontoxic glycosides for assaying glycogen synthesis enzymatic activity.

The assay method comprises incubating the sample with a composition comprising an alkyl glycoside having a nonreducing terminal glucose residue joined in α anomeric linkage, and radiolabeled UDP-glucose, followed by determining the presence of radioactivity incorporated into the alkyl glycoside, the presence of radioactivity indicating the presence of glycogen synthesis enzymatic activity in the sample. To limit the enzymatic activity measured to glycogenin, the concentration of UDP-glucose can be relatively low, for example, 10 μM or less, and the glucose-6-phosphate needed for the activation of glycogen synthase is omitted. To limit the enzymatic activity measured to glycogen synthase activity, the concentration can be relatively high, for example, 1 mM or greater, and glucose-6-phosphate (around 5–10 mM) is included.

The invention also provides a method of priming the incorporation of cellular glucose into an oligosaccharide in a cell comprising administering to the cell a priming amount of a membrane-permeating nontoxic glycoside having a suitable hydrophobic organic group joined by a linkage to a suitable hydrophilic saccharide, wherein the hydrophilic saccharide has a nonreducing terminal sugar residue selected from the group consisting of glucose or xylose, thereby priming the incorporation of cellular glucose onto the glycoside to form an oligosaccharide. Such priming of the incorporation of glucose into an oligosaccharide can be used to treat diabetes mellitus and glycogen storage disease, as described herein.

Glycosides useful for priming the incorporation of glucose into oligosaccharides have amphipathic properties due to their hydrophobic organic groups and their hydrophilic saccharide. These amphipathic properties enable them to readily penetrate cells chemically intact, so they have access to glycogenin and glycogen synthase. They can then serve as acceptors for the addition of multiple residues of glucose by these enzymes to create oligosaccharides having α(1→4) glycosidic linkages. Glycosides preferentially have up to around eight monosaccharide residues in order to readily permeate the cell.

Any compound chosen should be of minimal or nontoxicity to the cell, such as not to cause damage to the cell. Toxicity for any given compound may vary with the concentration of compound used. It is also beneficial if the compound chosen is metabolized or eliminated by the body and if this metabolism or elimination is done in a manner that will not be harmfully toxic.

The hydrophobic organic group can be, for example, an alkyl chain, an aralkyl group, an aryl group, or a steroid group. An alkyl chain can be chosen of any desired size, depending on the hydrophobicity desired and the hydrophilicity of the saccharide moiety. A preferred range of alkyl chains is from 8 to 14 carbon atoms. An aryl group can consist of, e.g., a phenyl group, a naphthyl group, an anthracene group, a phenanthrene group, or a flavonoid group. An aralkyl group can consist of, e.g., a benzyl group, a tolyl group, a 2-methylazulene group or a methylumbelliferyl group. A steroid group can be chosen from, for example, sapogenin, estradiol, cholesterol or cortisol.

The saccharide can be chosen, for example, from any currently commercially available saccharide species or can be synthesized. The saccharide can be a monosaccharide, a disaccharide, an oligosaccharide or a polysaccharide, or a combination thereof to form a saccharide chain. Some examples of the many possible saccharides to use include glucose, maltose, maltotriose, maltotetraose, sucrose and trehalose. One particularly useful saccharide would be one in which the end residue is xylose, as a compound comprising this structure would be more stable once administered and less susceptible to rapid hydrolytic cleavage by glycohydrolases such as α-glucosidase and amylase, and thus increase its therapeutic effect. Additionally, various oxygen atoms within the compounds can be substituted for by sulfur in order to decrease susceptibility to glycohydrolases. For example, the heteroatom of the sugar ring can be either oxygen or sulfur, or the linkage between monosaccharides in an oligosaccharide can be oxygen or sulfur. (Horton, D. and Wander, J. D., "Thio Sugars and Derivatives," *The Carbohydrates: Chemistry and Biochemistry*, 2d. Ed. Vol. IB, (W. Reyman and D. Horton eds.), pp. 799–842, (Academic Press, N.Y.), (1972)). Oligosaccharides can have either α (alpha) or β (beta) anomeric configuration but the linkage joining the last monosaccharide residue should preferably be in α anomeric configuration.

Many alkyl glycosides can be synthesized by known procedures, i.e., chemically, as described, e.g., in Rosevear et al., *Biochemistry* 19:4108–4115 (1980) or Koeltzow and Urfer, *J. Am. Oil Chem. Soc.*, 61: 1651–1655 (1984), U.S. Pat. No. 3,219,656 and U.S. Pat. No. 3,839,318 or enzymatically, as described, e.g., in Li et al., *J. Biol. Chem.*, 266:10723–10726 (1991) or Gopalan et al., *J. Biol. Chem.* 267:9629–9638 (1992). Many useful saccharides can be synthesized from a commercially available saccharide and UDP-glucose or UDP-xylose catalyzed by glycogenin, as described herein.

The linkage between the hydrophobic organic group and the hydrophilic saccharide can include, among other possibilities, a glycosidic, thioglycosidic (Horton), amide (*Carbohydrates as Organic Raw Materials*, F. W. Lichtenthaler ed., VCH Publishers, N.Y., 1991) carbon to carbon, or ester linkage (*Sugar Esters: Preparation and Application*, J. C. Colbert ed., (Noyes Data Corp., N.J.), (1974)).

Examples from which useful compounds can be chosen for the therapeutic composition include:

(a) a saccharide joined with an alkyl group: alkyl glycosides, such as octyl-, nonyl-, decyl-, undecyl-, dodecyl-, tridecyl-, tetradecyl, pentadecyl-, and octadecyl α- or β-D-maltoside, α-glucoside or -sucroside (linked to the fructose moiety of the sucrose) (synthesized according to Koeltzow and Urfer; Anatrace Inc., Maumee, Ohio; Calbiochem, San Diego, Calif.; Fluka Chemie, Switzerland); alkyl thiomaltosides, such as heptyl, octyl, dodecyl-, tridecyl-, and tetradecyl-β-D-thiomaltoside (synthesized according to Defaye, J. and Pederson, C., "Hydrogen Fluoride, Solvent and Reagent for Carbohydrate Conversion Technology" in *Carbohydrates as Organic Raw Materials*, 247–265 (F. W. Lichtenthaler, ed.) VCH Publishers, N.Y. (1991)); alkyl thioglucosides, such as heptyl- or octyl 1-thio α- or β-D-glucopyranoside (Anatrace, Inc., Maumee, Ohio; see Saito, S. and Tsuchiya, T. *Chem. Pharn. Bull.* 33:503–508 (1985)); alkyl maltotriosides (synthesized according to Koeltzow and Urfer); derivatives of palatinose and isomaltamine linked by amide linkage to an alkyl chain (synthesized according to Kunz, M., "Sucrose-based Hydrophilic Building Blocks as Intermediates for the Synthesis of Surfactants and Polymers" in *Carbohydrates as Organic Raw Materials*, 127–153); derivatives of isomaltamine linked by urea to an alkyl chain (synthesized according to Kunz); long chain aliphatic carbonic acid ureides of sucrose β-amino-alkyl ethers (synthesized according to Gruber and Greber,"Reactive Sucrose Derivatives" in *Carbohydrates as Raw Materials*, pp. 95–116); long chain aliphatic carbonic acid amides of sucrose β-amino-alkyl ethers (synthesized according to Austrian Patent 382,381 (1987), Chem. Abstr., 108:114719 (1988) and Gruber and Greber, pp. 95–116); alkyl glycosides provided by this invention, such as octyl-α-D-glucopyranosyl-α-D-xylopyranoside (synthesized from octyl-α-D-glucopyranoside and UDP-xylose catalyzed by glycogenin, as described herein), dodecyl-β-D-glucopyranosyl-α-D-glucopyranosyl-α-D-glucopyranosyl-α-D-glucopyranoside (dodecyl maltotetraoside) (synthesized from dodecyl-β-D-maltotrioside and UDP-glucose catalyzed by glycogenin, as described herein), dodecyl-β-D-glucopyranosyl-α-Dglucopyranosyl-α-D-xylopyranoside (synthesized from dodecyl-β-D-maltoside and UDP-xylose catalyzed by glycogenin); alkyl thioglycosides provided by this invention, such as octyl-1-thio-α-maltotrioside (synthesized from octyl-1-thio-α-maltoside and UDP-glucose, as described herein);

(b) a saccharide joined with an aryl group: phenyl α-D-glucopyranoside (synthesized according to Carbohydrates, P. M. Collins ed., p. 414 (Chapman and Hall, London, 1987)); 1-naphthyl α, β-maltoside (synthesized according to Matsubara, S. J., Biochem (Tokyo), 49:226–231 (1961)); phenyl sucrose (phenyl group linked to fructose moiety of sucrose) (synthesized according to Hough, L., Application of the Chemistry of Sucrose in *Carbohydrates as Organic Raw Materials*, 33–55); carminic acid (Natural Red 4) (Sigma Chemical Co., St. Louis, Mo.);

(c) a saccharide joined to an aralkyl group: 4-nonylumbelliferyl-α-glucoside (synthesized according to Bieberich, E. and Legler, G., *Biol. Chem.* Hoppe-Seyler, 370:809–817 (1989)); 2-hydroxymethyl-azulene glucopyranoside (synthesized according to Daub et al., "From Carbohydrates to Pigments: An Exercise in Molecular Material Science and Material Transformation," *Carbohydrate as Organic Raw Materials*, pp. 340–350).

(d) a saccharide joined to a fatty acid group: trehalose-6-mycolate (isolated according to Haferburg, et al., *Extracellular Microbial Lipids as Biosurfactants in Advances in Biochemical Engineering Biotechnology*, A. Fiechter, ed., Vol. 33, 53–93 (Springer-Verlag, Berlin, 1986)); stearyl sucrose (stearyl group linked to fructose moiety of sucrose) (manufactured by Mitsubishi Food Corp., Japan; derivatives synthesized according to Benson, F. R., Polyol Surfactants in *Nonionic Surfactants*, M. J. Schick, ed., pp. 247–299 (Marcel Dekker, N.Y., 1967) and references therein);

Some preferred glycosides include maltose, maltotriose, and maltotetraose linked by glycosidic linkage to an alkyl chain of 8, 10, 12 or 14 carbon atoms, i.e., octyl-, decyl-, dodecyl- and tetradecyl maltoside, maltotrioside, and maltotetraoside. These compositions are nontoxic, since they are degraded to an alcohol and an oligosaccharide, and amphipathic so they readily permeate cells. Also preferred are mixtures of glycosides wherein at least one glycoside in the mixture is optimal for priming glucose incorporation by glycogenin and at least one glycoside in the mixture is optimal for glycogen synthase.

The above examples are illustrative of the types of glycosides to be used in the methods claimed herein; the list is not exhaustive. Derivatives of the above compounds which fit the criteria of the claims should also be considered when choosing a glycoside. All of the compounds can be screened for efficacy following the methods taught in the examples.

The method can comprise administering, in addition to the glycoside, compounds and/or compositions that will also aid in relief of the symptoms of diabetes mellitus, such as proglycosyn, hypoglycemic agents (for example, tolbutamide and glyburide) and glucosidase inhibitors (for example, acarbose) as well as dietary or pharmacologic agents used in the treatment of glycogen storage disease. Dosages for the above-mentioned additional compounds are established and known to those skilled in the art (Kahn, C. R. et al., "Insulin, Oral Hypoglycemic Agents and the Pharmacology of the Exocrine Pancreas" in *The Pharmacological Basis of Therapeutics*, Goodman and Gilman 8th ed., pp. 1463–1495, Pergamon Press, N.Y. (1990)). Additionally, the composition can comprise the glycoside in liposome form, wherein the liposome contains an additional compound(s), as listed above.

Compounds for priming the incorporation of glucose into oligosaccharides are provided which comprise an alkyl glycoside having an 8 to 14 carbon alkyl chain joined by a linkage to a saccharide having from four to eight glucose residues. Such compounds are formed by the addition of glucose residues from UDP-glucose to a known alkyl glycoside by the glycogen synthesis enzymes, as described herein. Such compounds can also comprise an 8 to 14 carbon alkyl chain joined by a linkage to a saccharide having from one to eight glucose residues and a non-reducing terminal sugar residue consisting of xylose. Such a compound can be synthesized by the addition of glucose residues from UDP-glucose, by glycogenin or glycogen synthase, and the addition of a final xylose residue, by glycogenin, to a known alkyl glycoside. The linkages between each added monosaccharide residue will thus be $\alpha(1\rightarrow 4)$; the linkage between the alkyl chain and the first saccharide residue is determined by the chosen known starter alkyl glycoside. Preferable linkages include glycosidic and thioglycosidic linkages.

Compositions which can be used for treating diabetes are provided which comprise a compound useful for priming the incorporation of cellular glucose into an oligosaccharide, as described herein, and an additional antidiabetes agent, specifically, proglycosyn; a hyperglycemic agent, such as tolbutamide or glyburide; or a glucosidase inhibitor, such as acarbose.

The compounds or compositions may be administered orally, by inhalation, topically, parenterally (e.g., intravenously), by intramuscular injection, transdermally, or the like, although oral administration is typically preferred and intravenous administration is not recommended for compositions including acarbose. The amount of active compound administered will, of course, be dependent on the subject being treated, the subject's weight, the severity of symptoms, the manner of administration and the judgment of the prescribing physician. Generally, however, dosage will approximate that which is typical for the administration of compounds such as tolbutamide. Dosage optimally would be that required to reduce intracellular glucose levels, for example, to a normal range of about 5–6.7 mM.

Depending on the intended mode of administration, the pharmaceutical compounds or compositions may be in the form of solid, semi-solid or liquid dosage forms, such as, for example, tablets, suppositories, pills, capsules, powders, liquids, suspensions, aerosols, liposomes, lotions, creams, gels, or the like, preferably in unit dosage form suitable for single administration of a precise dosage. The compounds or compositions, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, triethanolamine sodium acetate, triethanolamine oleate, etc. Actual methods of preparing such dosage forms are known, or will be apparent, to those skilled in this art; for example, see *Remington's Pharmaceutical Sciences*, E. W. Martin, (ed.), Mack Publishing Co., Easton, Pa.

Liposomes can be prepared according to Szoka and Papahadjopoulos, *Ann. Rev. Biophys. Bioeng.*, 9:467 (1980) and Kiwada et al., *Chem. Pharm. Bull.* 33:753 (1985). The surfactant liposome can be administered without an additional permeability enhancing compound or as a carrier for an additional permeability enhancing compound. Liposomes can be administered, for example, orally or by aerosol inhalation.

For oral administration, fine powders or granules may contain diluting or dispersing agents, and may be presented in water or in a syrup, in capsules or sachets in the dry state, or in a nonaqueous solution or suspension, wherein suspending agents may be included, in tablets wherein binders and lubricants may be included, or in a suspension in water or a syrup (see, e.g., Weber, N. and Benning, H. *J Nutr.* 114:247–254 (1984)). Where desirable or necessary, flavoring, preserving, suspending, thickening, or emulsifying agents may be included. Tablets and granules may be coated.

For inhalation administration, the composition can be dissolved or dispersed in liquid form, such as in water or saline, preferably at a concentration at which the composition is fully solubilized and at which a suitable dose can be administered within an inhalable volume. Delivery can be repeated several times a day, depending upon the specific dosage chosen and the rate at which the chosen composition is cleared from the airways, with the goal being to reduce intracellular glucose levels.

Parenteral administration, if used, could also be by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

The exact amount of such compounds required will vary from subject to subject, depending on the species, age, and general condition of the subject, the severity of the disease that is being treated, the particular compound used, its mode of administration, and the like. Thus, it is not possible to specify an exact activity promoting amount. However, an appropriate amount may be determined by one of ordinary skill in the art using only routine testing given the teachings herein.

Any material added to the priming agent should be pharmaceutically acceptable. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained.

The present invention is more particularly described in the following examples which are intended as illustrative only since numerous modifications and variations therein will be apparent to those skilled in the art.

EXAMPLES

Glycogenin Assay

Glycogenin is a self-glycosylating glycosyltransferase which can be obtained from muscle and which can also be obtained from rat and beef kidney. The enzyme is capable of transferring glucose and xylose from the respective UDP-sugar substrates to itself and also of transferring these sugars to exogenous acceptors, such as dodecyl-β-D-maltoside, tetradecyl-β-D-maltoside, octyl-β-D-maltoside, octyl-α-D-glucoside and other glycosides, as described herein.

Fresh beef kidney was purchased from a local slaughter house. Purification of glycogenin from kidney involves the following steps: chromatography of a 105,000×g supernatant from a homogenate of beef kidney on DE-53 cellulose, chromatofocusing and chromatography on a column of UDP-glucuronic acid-agarose, which was eluted with cytidine 5'-diphosphate (CDP). This procedure resulted in an almost 38,000 fold purification of the enzyme after UDP-glucuronic acid-agarose chromatography. The protein concentration of the affinity purified enzyme was determined to be 10 µg/ml with the Quantigold protein reagent (Diversified Biotech, Newton Centre, Mass.).

The following materials were obtained from the sources indicated: EN$^3$HANCE, liquid and surface spray, UDP-[1-$^3$H] glucose (specific activity, 7.8 Ci/mmole or 11.7 Ci/mmole (kinetic studies only) and UDP-[1-$^3$H] xylose (specific activity, 8.9 Ci/mmole) DuPont (Boston, Mass.); SepPak $C_{18}$ cartridges (Millipore Corporation, Milford, Mass.); tetradecyl maltoside and dodecyl maltoside, Anatrace (Maumee, Ohio); octyl maltoside and dodecyl sucrose, Calbiochem (San Diego, Calif.); p-nitrophenyl maltoside, Boehringer Mannheim (Indianapolis, Ind.) and all other chemicals, Sigma (St. Louis, Mo.). Radioactivity was measured in a Wallac model 1410 liquid scintillation spectrometer.

An appropriate sample of UDP-[$^3$H] glucose or UDP-[$^3$H] xylose (supplied in 70% ethanol by the manufacturer) was evaporated to dryness with a gentle stream of filtered air and dissolved in 50 mM Tris Cl, pH 7.4/75 mM BAL/1.5 mM ATP. Reaction mixtures, in 1.5 ml polypropylene tubes, had a total of 75 µl and contained the following components: UDP-[$^3$H] glucose or UDP-[$^3$H] xylose (5 µl, 0.15 µCi), enzyme protein (19 µg of chromatofocusing purified or 10 ng of affinity purified enzyme), DBM (.01 mg/ml, 0.1 mg/ml, 1 mg/ml, 10 mg/ml, and 20 mg/ml) or other glycoside at such concentrations, and 50 mM Tris-Cl/6 mM $MnCl_2$/12 mM $MgCl_2$/5 mM BAL/0.1 mM ATP, pH 7.4, with either 2 mM CHAPS (TCA precipitation) or 1 mM CHAPS (SepPak $C_{18}$ isolation). After incubation for 60 min at 37° C. product formation was measured by either of the two procedures described below.

Product isolation by precipitation with trichloracetic acid. After completed incubation, 1% bovine serum albumin (50 µl) and 10% trichloracetic acid/4% phosphotungstic acid (150 µl) were added, and the mixture was vortexed and kept on ice for at least 15 min. The precipitate was sedimented by centrifugation in a microfuge and washed three times with 5% trichloroacetic acid. The bottom of the tube, containing the pellet, was clipped off with a dog nail clipper and dropped into a 6 ml scintillation vial, the protein was dissolved in 250 µl of 2M NaOH, and, after neutralization with 250 µl of 2M HCl, 4.5 ml of Ecolume was added, and the radioactivity was measured.

Product isolation by adsorption to SepPak $C_{18}$ cartridges. The reaction mixture was brought to a, volume of 0.5 ml by addition of water and was heated to 100° C. for 1 min. After cooling to room temperature, the mixture was centrifuged, and a 10 µl aliquot was removed for measurement of total radioactivity. The remaining 490 µl was applied with the use of a 10 ml syringe to a SepPak $C_{18}$ cartridge, which had been preconditioned by washing with 8 ml of 95% ethanol, 8 ml of 70% ethanol, and 20 ml of water. After sample application, the cartridge was washed with 2×9 ml of water, followed by an additional 2 ml portion of water, and adsorbed radioactive material was then eluted with 3×4 ml of 70% ethanol. Typically, no significant radioactivity was found in the last water wash, and most of the bound radioactive material was found in the first ethanol eluate.

Gel electrophoresis and autoradiography. SDS-PAGE was carried out with slight modification of Laemmli (Laemmli, U. K., *Nature,* 227:680–685 (1970)). A Hoefer vertical slab gel electrophoresis unit (Hoefer Scientific Instruments, San Francisco, Calif.) was used for casting and electrophoresing with a 10% (w/v) acrylamide separating gel and a 4.5% (w/v) acrylamide stacking gel. Reaction mixtures, with total volumes of 75 µl, containing 0.15 µCi (0.26 µM) UDP-[$^3$H] glucose, 10 ng of affinity purified enzyme (intact or heat denatured), in the absence and presence of increasing concentrations of DBM were incubated at 37° C. for 60 min. The reaction was terminated by addition of 5 µl of water and 20 µl of sample reducing buffer (5× concentrated) to give final concentrations of 40 mM Tris-Cl, pH 6.8, 1.5% (w/v) SDS, 6% (v/v) glycerol, 100 mM DTT and 0.002% (w/v) bromophenol blue and heated to 100° C. for 3 min. The supernatant was applied to the gel and electrophoresed at 7.5 mA for 16 hours. The gel was soaked in EN$^3$HANCE, dried and autoradiography was performed using Kodak AR film (Eastman Kodak, Rochester, N.Y.) at −70° C.

Inhibition of glucose transfer to DBM by cytidine 5'-diphosphate. It has been shown previously that cytidine 5'-diphosphate is a potent inhibitor of the self-glucosylation of glycogenin (Manzella et al., *The Pharmacologist,* 33:206 (1991)). It has now been determined that this is also true for the transfer to exogenous acceptor. Cytidine 5'-diphosphate (0.1–0.5 mM) inhibited the transfer of [$^3$H]glucose to DBM by glycogenin in a dose dependent manner.

Results with DBM. Glycogenin transfers glucose from UDP-glucose to dodecyl-β-D-maltoside (DBM) in a dose-dependent fashion as the concentration of the acceptor substrate is increased from 0.0001–10 mg/ml DBM. The enzymatic transfer of glucose from UDP-glucose to DBM by glycogenin is dependent on the amount of enzyme protein present (0.1–0.4 µg/ml), the time of incubation (0–150 minutes) and the concentration of the donor substrate UDP-glucose (0–15 µM). Transfer of glucose to DBM by glycogenin can be demonstrated by three different independent assay procedures: TCA precipitation, adsorption to SepPak $C_{18}$ and biphasic liquid scintillation counting. That the transfer is dependent on both the presence of enzyme and DBM is indicated by the markedly reduced amount or absence of product in incubation mixtures lacking enzyme or DBM (0.1 mM or 0.2 mM). That glycogenin is the enzyme catalyzing the transfer of glucose from UDP-glucose to DBM is indicated by the dose-dependent inhibition of this reaction with CDP, a nucleotide which we have shown to be a potent inhibitor of glycogenin. Therefore DBM is capable of acting as an artificial acceptor substrate for glucose transfer from UDP-glucose by glycogenin. This results in a marked increase in the amount of glucose that can be transferred in the presence of enzyme alone by self-glycosylation and therefore makes DBM valuable in conditions where increased disposal of excess glucose is beneficial, e.g., diabetes mellitus. Furthermore, by providing many more primer sites for de novo synthesis of glucose chain molecules, DBM can be used to treat glycogen storage disease by creating more molecules of a much smaller and more manageable size, rather than the accumulation of large glycogen molecules that characterize this disease.

Characterization of the Product of Transfer. Size exclusion chromatography of a reaction mixture containing DBM showed much more $^3$H-glucose radiolabeled product eluting in the void volume ($V_o$) of a Sephadex G-50 column than identical chromatography of a reaction mixture lacking DBM.

That this increased product formation represented transfer of [$^3$H]-glucose to DBM rather than self-glycosylation by glycogenin was indicated by electrophoresis of standard reaction mixtures containing increasing amounts of DBM on SDS-polyacrylamide gels. Autoradiography of the resulting gel showed a decrease of [$^3$H]-glucose incorporation into the 32–38 kDa products representing glycogenin as the DBM in the reaction mixture was increased, and an increase in incorporation into a radiolabeled product which moved at the bottom of the gel and represented DBM to which $^3$H-glucose had been transferred. This product was identified as DBM-glucose by thin layer chromatography and autoradiography of the reaction mixture which had first been passed through a SepPak $C_{18}$ cartridge and eluted with 70% ethanol to separate the labeled product from unreacted and degraded UDP-[$^3$H]glucose substrate. The formation of DBM-glucose (dodecyl-β-D-maltotrioside) was further demonstrated by separation of the new product from the DBM starting material by high pressure liquid chromatography. When UDP-[$^3$H]xylose was used as the starting donor substrate, then DBM-xylose was formed (dodecyl-β-D-glucosyl-α-(1→4)glucosyl-α-(1→4)xyloside). Under appropriate reaction conditions (low DBM concentration, longer incubation times), more than one glucose residue could be transferred to DBM to form DBM-glucose-glucose (dodecyl-β-D-maltotetraoside). Synthesis of this compound was also demonstrated by its separation from DBM and dodecyl-β-maltotrioside on high pressure liquid chromatography. By isolating the newly formed products by HPLC and reincubating them with glycogenin and UDP-glucose, it is possible to form products containing larger oligosaccharides attached to DBM, i.e., dodecyl-β-D-maltopentaoside, dodecyl-β-D-maltohexaoside, etc. Each of these products represents a new compound which may potentially serve as an acceptor substrate for glycogenin and/or glycogen synthase. Therefore, under appropriate conditions, DBM is capable of serving as an acceptor for several glucose and/or xylose residues producing dodecyl-oligosaccharide products, which can serve as further substrates for glycogenin and/or glycogen synthase demonstrating the ability of this compound to facilitate disposal of excess glucose into glycogen-like products.

Results with other alkyl glycosides. Other alkylglycosides were also capable of serving as acceptor substrates for the transfer of glucose and xylose from their respective UDP-sugar donor substrates by glycogenin. These included octyl-β-D-maltoside, decyl-β-D-maltoside and tetradecyl-β-D-maltoside which all could be converted to their respective maltotriosides by addition of one glucose residue. Of these substrates, DBM was the best acceptor for glucose, being twice as active as tetradecyl-β-D-maltoside and four times better than octyl-β-D-maltoside. In contrast dodecyl-β-D-sucrose showed a much lower activity as a glucose acceptor indicating the importance of the saccharide moiety in the activity of the alkyl glycosides. Most importantly, DBM was 29 times more effective as a glucose acceptor than p-nitrophenyl-α-maltoside, the best exogenous acceptor for glycogenin reported prior to this invention. In addition, DBM and the other alkylglycosides are metabolized to nontoxic products, whereas, metabolism of p-nitrophenyl-α-maltoside, would give rise to the toxic p-nitrophenol. Octyl-α-D-glucoside also served as an effective glucose acceptor for glycogenin and was much better in this regard than octyl-β-D-glucoside and octyl-β-D-thioglucoside, showing the importance of the α-linkage of the carbohydrate to the alkyl moiety when alkyl monosaccharides are used as acceptors. It should be noted that this linkage is of much less importance when examining the activity of alkyl disaccharides, such as dodecylmaltoside; the β-linked compound (DBM) is the most active compound thus far tested, and the α-linked compound would be expected to have equal or greater activity. Note also that even though the activities are low, octyl-β-D-thioglucoside is more active as a glucose acceptor than octyl-β-D-glucoside, indicating that substitution of a thioether for the ether linkages in the alkylglycosides would likely make them better acceptors as well as more resistant to enzymatic degradation.

Glycogen Synthase Assay

The assay of glycogen synthase in vitro depends on the presence of polymeric glycogen as an acceptor for glucose transfer. Oligosaccharides such as maltose, maltotriose and maltotetraose serve as substrates for glycogenin and as primers for glycogen synthase but have only a low affinity for these enzymes. Glycosides, on the other hand, in addition to serving as an acceptor substrate for glucose and xylose transfer by glycogenin, can also serve as a glucose acceptor for transfer catalyzed directly by glycogen synthase and are active in stimulating the synthesis of glycogen-related oligosaccharides linked to the starter glycoside.

Rabbit muscle glycogen synthase obtained from Sigma Chemical Co., (7.6 μg) was incubated with 0.45 μCi UDP-[$^3$H]glucose (specific activity of 10.4 Ci/mmol), 1 mM UDP-glucose (glucose donor), 10 mM glucose-6-phosphate (the natural activator of glycogen synthase) and 1 mg glycogen (glucose acceptor) in 25 mM EDTA/5 mM DTT/100 mM glycine. NaOH buffer, pH 8.6 in a total volume of 100 μl for 30–240 minutes at 37° C. At different time points, glycogen was precipitated from the reaction mixtures with ethanol and the precipitate washed to remove any unincorporated radiolabel. The glycogen precipitate was then solubilized and counted in a liquid scintillation counter to quantitate the amount of [$^3$H]glucose incorporated into glycogen. By this method, glucose transfer to glycogen can be demonstrated.

Results. When DBM (0.5 mM) replaces glycogen as the glucose acceptor in the incubation mixture, a linear transfer of glucose to DBM with time is seen up to 4 hours, with the glucose transfer amounting to about 20% of the maximal value seen with glycogen (using the SepPak $C_{18}$ assay). It should be noted however, that the glucose transfer to DBM showed no signs of plateauing at 4 hours incubation time and that longer incubation would have resulted in even greater glucose transfer to DBM. When glycogen synthasecatalyzed glucose transfer to DBM was plotted as a function of the acceptor substrate, i.e., from 0.1 to 10 mM DBM for a 60 min incubation, near-maximal activity was seen at less than 0.5 mM DBM, indicating that this substrate has a high affinity for glycogen synthase. In these experiments glucose transfer to DBM was totally dependent on the presence of glucose-6-phosphate (G-6-P), indicating that under these conditions it was mediated by glycogen synthase and not by glycogenin, since G-6-P activates only the former enzyme. Interestingly, when octyl-, dodecyl-, and tetradecyl- maltosides were compared under these conditions, transfer of glucose to all three acceptor substrates was dependent on G-6-P, and octylmaltoside proved to be the best acceptor, followed by DBM and tetradecylmaltoside. Therefore, the glucose acceptor specificities of glycogenin and glycogen synthase differ somewhat so that mixtures of alkylglycosides, e.g., octylmaltoside and dodecylmaltoside may prove optimum in serving as initiators of glycogen synthesis enzymatic activity and glucose acceptor substrates for both enzymes.

Of the greatest importance is the demonstration that DBM can serve as an acceptor for glucose addition by glycogen synthase to produce DBM-linked oligosaccharides which are greater than seven glucose residues in length, showing that this compound can act as a reservoir for glucose disposal. When glycogen synthase was incubated for 24 hours with G-6-P, UDP-[$^3$H]glucose and 0.5 mM DBM, several products of glucose transfer to DBM could be visualized following separation by thin layer chromatography and autoradiography. These products corresponded to the dodecyl-maltotrioside, -tetraoside, -pentaoside, -hexaoside, -heptaoside and higher oligosaccharide derivatives of DBM. Note that considerably more product is seen at the origin of the TLC plate in the incubation mixture containing DBM than in that lacking it, indicating that glucose incorporation into DBM-linked products with greater than seven glucose residues is appreciable. Therefore, DBM and other suitable glycosides can serve as glucose acceptors for both glycogen synthase and glycogenin to promote glucose disposal in conditions such as hyperglycemia and diabetes mellitus. Providing an abundance of acceptor substrates in tissues, such as liver, which has a smaller number of extremely large glycogen molecules can alleviate the problem of excessive glycogen deposition in the glycogen storage diseases by promoting glucose disposal into more readily handled smaller glucose polymers built on DBM or other glycosides.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method of treating diabetes mellitus or glycogen storage disease by increasing the incorporation of cellular glucose into an oligosaccharide in a cell, comprising;

administering to a patient in need thereof a therapeutically effective amount of a composition consisting essentially of a membrane-permeating nontoxic-glycoside having a hydrophobic organic group joined by a linkage to a hydrophilic saccharide, wherein the hydrophilic saccharide is a mono, di-, or tri- saccharide and has a nonreducing terminal sugar residue selected from the group consisting of glucose or xylose so as to increase the incorporation of cellular glucose into an oligosaccharide in a cell.

2. The method of claim 1, wherein the monosaccharide residues are selected from the group consisting of glucose and xylose.

3. The method of claim 1, wherein the linkage is selected from the group consisting of a glycosidic linkage, a thioglycosidic linkage, an amide linkage, a ureide linkage, a carbon to carbon linkage and an ester linkage.

4. The method of claim 1, wherein the nonreducing terminal sugar is joined in α anomeric linkage.

5. The method of claim 1, wherein the saccharide has a ring structure containing at least one sulfur atom.

6. The method of claim 1, wherein the monosaccharide residues of the saccharide are linked by a series of sulfur atoms, one between each of the monosaccharide residues.

7. The method of claim 1, wherein the organic group is selected from the group consisting of alkyl, aralkyl, aryl and steroid.

8. The method of claim 1, wherein the glycoside is an alkyl glycoside.

9. The method of claim 8, wherein the alkyl group of the alkyl glycoside has from four to twenty carbon atoms.

10. The method of claim 8, wherein the saccharide of the alkyl glycoside is selected from the group consisting of glucose, maltose and maltotriose.

11. The method of claim 10, wherein the alkyl group has from 8 to 14 carbon atoms.

12. The method of claim 1, wherein the glycoside is administered orally.

13. The method of claim 12, wherein the glycoside is an alkyl glycoside.

14. The method of claim 13, wherein the alkyl glycoside is an alkyl maltoside.

15. The method of claim 1, wherein the hydrophilic saccharide is a monosaccharide.

16. The method of claim 1, wherein the hydrophilic saccharide is a disaccharide.

17. The method of claim 1, wherein the hydrophilic saccharide is a trisaccharide.

* * * * *